United States Patent
Matsui et al.

(10) Patent No.: US 7,183,375 B2
(45) Date of Patent: Feb. 27, 2007

(54) INHIBITORS FOR CONTINUOUS ACTIVATION FOR CALCINEURIN

(75) Inventors: Hideki Matsui, 139-11-501, Higashiune, Okayama-shi, Okayama (JP) 701-0211; Kazuhito Tomizawa, 14-7-604, Higashifurumatsu 1-chome, Okayama-shi, Okayama (JP) 700-0921

(73) Assignees: Agencey of Industrial Science and Technology, Saitama (JP); Hideki Matsui, Okayama (JP); Kazuhito Tomizawa, Okayama (JP)

( * ) Notice: Subject to any disclaimer, the term of this patent is extended or adjusted under 35 U.S.C. 154(b) by 125 days.

(21) Appl. No.: 10/518,710

(22) PCT Filed: Oct. 7, 2003

(86) PCT No.: PCT/JP03/12816

§ 371 (c)(1),
(2), (4) Date: Dec. 22, 2004

(87) PCT Pub. No.: WO2004/032955

PCT Pub. Date: Apr. 22, 2004

(65) Prior Publication Data

US 2006/0177431 A1    Aug. 10, 2006

(30) Foreign Application Priority Data

Oct. 8, 2002    (JP) ............................. 2002-294815

(51) Int. Cl.
*A61K 38/10* (2006.01)
*A61K 38/16* (2006.01)
(52) U.S. Cl. ...................................... 530/326; 530/324
(58) Field of Classification Search ................... None
See application file for complete search history.

(56) References Cited

FOREIGN PATENT DOCUMENTS

WO    WO 02/00872 A2    1/2002

OTHER PUBLICATIONS

User Protocol208733 Rev. 11 for the Calpain Inhibitor Set, Calibochem, 2006 http://www.emdbiosciences.com/product/208733.*
Hosfield et al. "Crystal structure of calpain reveals the structural basis for Ca2+-dependent protease activity and a novel mode of enzyme activation," EMBO J., 1999, 18, 6880-9.*
Ginalski et al. "Practical lessons from protein structure prediction." Nuc. Ac. Res., 2005, 33, 1874-1891.*
Rudinger "Characteristic of the amino acids as components of a peptide hormone sequence." (Peptide Hormones (Ed. J.A. Parson). University Park Press. Baltimore, 1976, pp. 1-7.*
Pitt et al. "Single amino acid substitution mutants of *Klebsiella pneumoniae* singma54 defective in transcription" Nuc. Ac. Res., 2000, 28, 4419-4427.*
Bradley et al. "Limits of Cooperativity in a Structurally Modular Protein: Response of the Notch Ankyrin Domain to Analogous Alanine Substitutions in Each Repeat" J. Mol. Biol., 2002, 324, 373-386.*
Flanagan et al. "Truncated staphyloccal nuclease is compact but disordered" Proc. Natl. Acad. Sci. USA, 1992, 89, 748-752.*
Sawai et al. "Impact of single-residue mutations on the structure and function of ovispirin/novispirin antimicrobial peptides" Prot. Engin., 2002, 15, 225-232.*
Schnog et al. "Sickle cell disease; a general overview" J. Med., 2004, 62, 364-374.*
Asai, A. et al., "High Level Calcineurin Activity Predisposes Neuronal Cells to Apoptosis", J. Biol. Chem., (1999), vol. 274, No. 48, pp. 34450-34458.
Matsui, H. et al., "Saibo no Kino Seigyo to Calcium Seminar Calcineurin no Kozo to Kino", Clinical Calcium, (1993), vol. 3, No. 11, pp. 58-63.
Kim, M. J. et al., "Calpain-dependent cleavage of cain/cabin1 activates calcineurin to mediate calcium-triggered cell death", Proc. Natl. Acad. Sci. USA, (Jul. 2002), vol. 99, No. 15, pp. 9870-9875.
Morioka, M. et al., "Potential Role of Calcineurin for Brain Ischemia and Traumatic Injury", Prog. Neurobiol., (1999), vol. 58, No. 1, pp. 1-30.
Springer, J. E. et al., Calcineurin-Mediated BAD Dephosphorylation Activates the Capsase-3 Apoptotic Cascade in Traumatic Spinal Cord Injury, J. Neurosci., (2000), vol. 20, No. 19, pp. 7246-7251.
Tallant, E.A. et al., "Activation of a Calmodulin-Dependent Phosphatase by a $Ca^{2+}$-Dependent Protease", Biochemistry, (1988), vol. 27, No. 6, pp. 2205-2211.

* cited by examiner

*Primary Examiner*—Cecilia J. Tsang
*Assistant Examiner*—Christina M. Bradley
(74) *Attorney, Agent, or Firm*—Browdy and Neimark, PLLC

(57) ABSTRACT

The object of the present invention is to provide a suppressant for neuronal cell death effective for various diseases which inhibits a constitutive active forming of calcineurin and has less side effect. An inhibitor of constitutive active forming of calcineurin, more specifically a drug which inhibits cleavage of calcineurin subunit A (CaNA) by calpain. Examples thereof include peptides having the amino acid sequence of FDGATAAARKEVIRNK (SEQ No. 1) and REESESVLTLKGLTPTG (SEQ No. 2).

4 Claims, 2 Drawing Sheets

```
                         SEQUENCE LISTING

<160> NUMBER OF SEQ ID NOS: 6

<210> SEQ ID NO 1
<211> LENGTH: 16
<212> TYPE: PRT
<213> ORGANISM: human

<400> SEQUENCE: 1

Phe Asp Gly Ala Thr Ala Ala Arg Lys Glu Val Ile Arg Asn Lys
 1               5                  10                  15

<210> SEQ ID NO 2
<211> LENGTH: 17
<212> TYPE: PRT
<213> ORGANISM: human

<400> SEQUENCE: 2

Arg Glu Glu Ser Glu Ser Val Leu Thr Leu Lys Gly Leu Thr Pro Thr
 1               5                  10                  15

Gly

<210> SEQ ID NO 3
<211> LENGTH: 521
<212> TYPE: PRT
<213> ORGANISM: human

<400> SEQUENCE: 3

Met Ser Glu Pro Lys Ala Ile Asp Pro Lys Leu Ser Thr Thr Asp Arg
 1               5                  10                  15

Val Val Lys Ala Val Pro Phe Pro Pro Ser His Arg Leu Thr Ala Lys
                20                  25                  30

Glu Val Phe Asp Asn Asp Gly Lys Pro Arg Val Asp Ile Leu Lys Ala
            35                  40                  45

His Leu Met Lys Glu Gly Arg Leu Glu Glu Ser Val Ala Leu Arg Ile
        50                  55                  60

Ile Thr Glu Gly Ala Ser Ile Leu Arg Gln Glu Lys Asn Leu Leu Asp
 65                  70                  75                  80

Ile Asp Ala Pro Val Thr Val Cys Gly Asp Ile His Gly Gln Phe Phe
                85                  90                  95

Asp Leu Met Lys Leu Phe Glu Val Gly Gly Ser Pro Ala Asn Thr Arg
            100                 105                 110

Tyr Leu Phe Leu Gly Asp Tyr Val Asp Arg Gly Tyr Phe Ser Ile Glu
        115                 120                 125

Cys Val Leu Tyr Leu Trp Ala Leu Lys Ile Leu Tyr Pro Lys Thr Leu
    130                 135                 140

Phe Leu Leu Arg Gly Asn His Glu Cys Arg His Leu Thr Glu Tyr Phe
145                 150                 155                 160

Thr Phe Lys Gln Glu Cys Lys Ile Lys Tyr Ser Glu Arg Val Tyr Asp
                165                 170                 175
```

-continued

```
Ala Cys Met Asp Ala Phe Asp Cys Leu Pro Leu Ala Ala Leu Met Asn
            180                 185                 190

Gln Gln Phe Leu Cys Val His Gly Gly Leu Ser Pro Glu Ile Asn Thr
        195                 200                 205

Leu Asp Asp Ile Arg Lys Leu Asp Arg Phe Lys Glu Pro Pro Ala Tyr
    210                 215                 220

Gly Pro Met Cys Asp Ile Leu Trp Ser Asp Pro Leu Glu Asp Phe Gly
225                 230                 235                 240

Asn Glu Lys Thr Gln Glu His Phe Thr His Asn Thr Val Arg Gly Cys
            245                 250                 255

Ser Tyr Phe Tyr Ser Tyr Pro Ala Val Cys Asp Phe Leu Gln His Asn
        260                 265                 270

Asn Leu Leu Ser Ile Leu Arg Ala His Glu Ala Gln Asp Ala Gly Tyr
    275                 280                 285

Arg Met Tyr Arg Lys Ser Gln Thr Thr Gly Phe Pro Ser Leu Ile Thr
290                 295                 300

Ile Phe Ser Ala Pro Asn Tyr Leu Asp Val Tyr Asn Asn Lys Ala Ala
305                 310                 315                 320

Val Leu Lys Tyr Glu Asn Asn Val Met Asn Ile Arg Gln Phe Asn Cys
            325                 330                 335

Ser Pro His Pro Tyr Trp Leu Pro Asn Phe Met Asp Val Phe Thr Trp
        340                 345                 350

Ser Leu Pro Phe Val Gly Glu Lys Val Thr Glu Met Leu Val Asn Val
    355                 360                 365

Leu Asn Ile Cys Ser Asp Asp Glu Leu Gly Ser Glu Glu Asp Gly Phe
    370                 375                 380

Asp Gly Ala Thr Ala Ala Ala Arg Lys Glu Val Ile Arg Asn Lys Ile
385                 390                 395                 400

Arg Ala Ile Gly Lys Met Ala Arg Val Phe Ser Val Leu Arg Glu Glu
                405                 410                 415

Ser Glu Ser Val Leu Thr Leu Lys Gly Leu Thr Pro Thr Gly Met Leu
            420                 425                 430

Pro Ser Gly Val Leu Ser Gly Lys Gln Thr Leu Gln Ser Ala Thr
        435                 440                 445

Val Glu Ala Ile Glu Ala Asp Glu Ala Ile Lys Gly Phe Ser Pro Gln
    450                 455                 460

His Lys Ile Thr Ser Phe Glu Glu Ala Lys Gly Leu Asp Arg Ile Asn
465                 470                 475                 480

Glu Arg Met Pro Pro Arg Arg Asp Ala Met Pro Ser Asp Ala Asn Leu
                485                 490                 495

Asn Ser Ile Asn Lys Ala Leu Ala Ser Glu Thr Asn Gly Thr Asp Ser
            500                 505                 510

Asn Gly Ser Asn Ser Ser Asn Ile Gln
        515                 520
```

<210> SEQ ID NO 4
<211> LENGTH: 11
<212> TYPE: PRT
<213> ORGANISM: HIV virus

<400> SEQUENCE: 4

```
Tyr Gly Arg Lys Lys Arg Arg Gln Arg Arg Arg
 1               5                  10
```

<210> SEQ ID NO 5

-continued

```
<211> LENGTH: 26
<212> TYPE: PRT
<213> ORGANISM: human

<400> SEQUENCE: 5

Arg Arg Arg Arg Arg Arg Arg Arg Arg Arg Phe Asp Gly Ala Thr Ala
 1               5                  10                  15

Ala Ala Arg Lys Glu Val Ile Arg Asn Lys
            20                  25

<210> SEQ ID NO 6
<211> LENGTH: 27
<212> TYPE: PRT
<213> ORGANISM: human

<400> SEQUENCE: 6

Arg Arg Arg Arg Arg Arg Arg Arg Arg Arg Arg Glu Glu Ser Glu Ser
 1               5                  10                  15

Val Leu Thr Leu Lys Gly Leu Thr Pro Thr Gly
            20                  25
```

INHIBITORS FOR CONTINUOUS ACTIVATION FOR CALCINEURIN

TECHNICAL FIELD

The present invention relates to an inhibitor of constitutive active forming of calcineurin. The present invention more specifically relates to a drug which inhibits cleavage of calcineurin subunit A (CaNA) by calpain.

BACKGROUND ART

Calcineurin is a phosphatase which is activated depending on calcium and calmodulin. It is a complex consisting of calcineurin subunit A (CaNA) having a catalytic center and calcineurin subunit B (CaNB) being a regulating factor. Calcineurin usually exists in an unactive form in the cell, because the association of the catalytic center with a substrate is obstructed by the autoinhibitory domain. The increased intracellular concentration of calcium leads to open the autoinhibitory domain by changing the structure of calcineurin (active form) which results in that the substrate can be associated with the catalytic center. Meanwhile, the decreased intracellular concentration of calcium leads calcineurin to return to the unactive form again. As just described, it is known in the prior art that calcineurin is reversibly activated depending on the concentration of calcium.

In 1999, it was reported that calcineurin played an important role in neuronal cell death (refer to Asai Akio, et al., J. Biological Chemistry, Vol. 274. p. 34450, 1999). Furthermore, it has been also reported that the calcineurin-specific inhibitor (immunosuppressants; FK506 and cyclosporin A) suppresses neuronal cell death (refer to Morioka Motohiro, et al., Progress in Neurobiology, Vol. 58, p. 1, 1999; and Springer Joe E., et al., The Journal of Neuroscience, Vol. 20, p. 7246, 2000). On the basis of many reports including such literatures, as a mechanism of neuronal cell death observed in brain ischmia and spinal injury, it has been suggested now that N-methyl-D-asparginic acid receptor (NMDA receptor), which is one of the glutamic acid receptors, is abnormally activated by the excitation of the neuronal cell followed by an influx of large quantity of calcium into the cell through the receptor, and thereby calcineurin is activated to induce cell death. However, since the influx of calcium is transient, the activated state of calcineurin does not continue for a long term. Therefore, although it is imaged that there is any other mechanism by which calcineurin is activated for the long term than the transient increase of intracellular concentration of calcium, such mechanism has never been reported.

As mentioned above, it is known that immunosuppressants FK506 and cyclosporine A have a suppressive effect on neuronal cell death, in particular ischemic and excitatory neuronal cell death. However, it is known that the side effect of such agents is large (for example, toxicity, diabetes and the like), because the agents suppress all signal transduction involved in calcineurin. Therefore, a suppressant for neuronal cell death which can inhibit a long term activation of calcineurin and show less side effect compared with the conventional one is strongly desired.

DISCLOSURE OF INVENTION

The objects of the present invention are to solve the above-mentioned problems and to provide a suppressant for neuronal cell death having less side effect and which is effective for treating various diseases.

As a result of intensive investigations to solve the above-mentioned problems, the following findings were obtained.

a) When neuronal cell death was induced with administering glutamic acid, the fragmentation of calcineurin subunit A (CaNA) was observed.

b) Cleavage sites of CaNA were between amino acid residues of 392 (arginine) and 393 (lysine) and between amino acid residues of 421 and 425 in the amino acid sequence.

c) It was clarified that calcineurin had an activity independent of calcium and calmodulin, when it was cleaved at said sites.

d) Said fragmentation was caused by calpain, which had thought to belong to a different signal transduction route from calcineurin, and inhibited by a calpain inhibitor.

e) When the peptide including amino acid residues 392–393 or amino acid residues 421–425 of CaNA was introduced in the neuronal cell, neuronal cell death by glutamic acid administration was suppressed.

On the basis of the above-mentioned findings we have discovered a cell death suppressant targeting the mechanism of the long term activation of calcineurin but not the calcineurin activation through the transient increase of the intracellular concentration of calcium, and have established the present invention. That is, this invention relates to;

(a) an inhibitor for cleavage of CaNA by calpain, comprising the peptide of SEQ No. 1, the peptide of SEQ No. 2 and/or analogues thereof;

(b) a suppressant for neuronal cell death comprising the inhibitor for cleavage of CaNA of the above (a) as an active ingredient;

(c) a suppressant for progress of a disease associated with dementia comprising the inhibitor for cleavage of CaNA of the above (a) as an active ingredient; and (d) an additive for a culture medium of cells and brain slice comprising the inhibitor for cleavage of CaNA of the above (a).

BRIEF DESCRIPTION OF DRAWINGS

FIG. 1 is photographs showing cleavage of CaNA on inducing neuronal cell death with the addition of glutamic acid, and the inhibitory effect of the CaNA inhibitor of the present invention on cleavage of CaNA. In FIGS. 1(a) and (b), lane 1 shows a control, lane 2 the sample in which glutamic acid was added alone, lane 3 the sample in which the cleavage inhibiting peptide was added alone, and lane 4 the sample in which glutamic acid and the cleavage inhibiting peptide were added.

BEST MODE FOR CARRYING OUT THE INVENTION

Figure 1A:
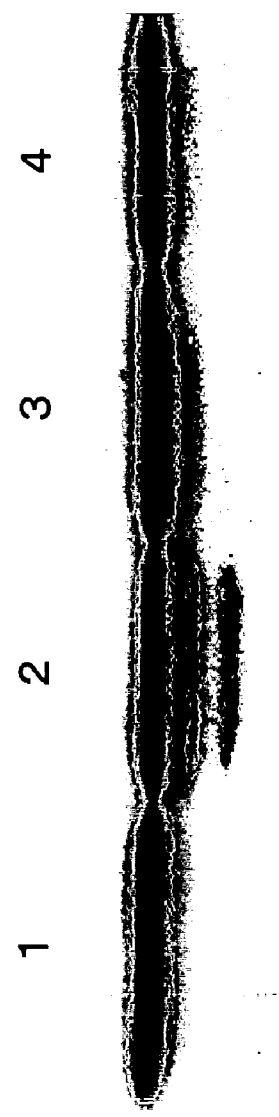
FIG. 1(a) shows the result of the sample which was incubated for 3 hours after the addition of glutamic acid.

The inhibitor for cleavage of calcineurin subunit A (CaNA: SEQ No. 3) by calpain means a substance comprising the peptide of SEQ No. 1, the peptide of SEQ No. 2 and/or an analogue thereof, which inhibits cleavage of CaNA at between amino acid residues 392 and 393 or 421 and 425, and resulting in the inhibition of constitutive active forming of calcineurin.

The above-mentioned analogue of the peptide of SEQ No. 1 includes a peptide comprising amino acid sequence of the peptide of SEQ No. 1 which is deleted, substituted a part thereof and/or another amino acid sequence is inserted or added at the terminal of the peptide, and which inhibits cleavage of CaNA by calpain. For example, a peptide in which the amino acid residue 9 is changed from Arg to Lys and/or a peptide in which the amino acid residue 10 Lys is changed to Arg in the peptide of SEQ No. 1 is included in the analogues of the peptide of SEQ No. 1 of the present invention.

The above-mentioned analogue of the peptide of SEQ No. 2 includes a peptide comprising amino acid sequence of the peptide of SEQ No. 2 which is deleted, substituted a part thereof and/or another amino acid sequence is inserted or added at the terminal of the peptide, which inhibits cleavage of CaNA by calpain. For example, a peptide in which the amino acid residue 11 Lys is changed to Arg in the peptide of SEQ No. 2 is included in the analogues of the peptide of SEQ No. 2 of the present invention.

An inhibitory activity of the analogue of the peptide of SEQ No. 1 or 2 (analogue peptide) for cleavage of CaNA can be evaluated by the following manner. That is, the test solution (0.1 µM or 10 µM of analogue peptide, 5 µM purified calpain, 20 mM Tris-HCl (pH 7.4) and 1 mM $CaCl_2$) is prepared and then purified calcineurin is added thereto and incubated at 30° C. for 1 hour. The reaction solution is elctrophoresed on a gel with 10% SDS-PAGE, and is stained with Coomassie blue. The evaluation can be performed by determining the quantity of calpain dependent fragmentated calcineurins which are found as molecular weights of 45 kDa and 48 kDa as the result of the stain.

The above-mentioned peptides can be prepared by using a known method such as solid phase or liquid phase synthesis with Boc or Fmoc strategy. The obtained peptide after that manner can be also purified with a known method such as ether precipitation/filtration, high performance liquid chromatography (HPLC) or perfusion chromatography.

The inhibitor for cleavage of CaNA by calpain of the present invention can contain an additional compound as long as it contains the peptide of SEQ No. 1, the peptide of SEQ No. 2 and/or the analogue thereof. The additional compound includes, for example, an intracellular transporting signal peptide consisting of 7 to 30 amino acid residues which contains 50% or more arginine or lysine thereof, such as a polyarginine peptide (for example, polyarginine peptide consisting of five arginine residues), protein transporting domain (PTD; SEQ No. 4) consisting of 11 amino acid residues which is contained in TAT protein of HIV virus; or linear polyethylenimine (PEI) being a cationic water-soluble polymer. Such compound can be associated with (or fused to) the peptide of SEQ No. 1, the peptide of SEQ No. 2 and/or the analogue thereof by using a method such as (i) to be synthesized starting with the peptide of SEQ No. 1, the peptide of SEQ No. 2 and/or the analogue thereof using general peptide synthesis, or (ii) one peptide is bound to a divalent crosslinking agent, a terminal of another peptide is bound to a cysteine residue, and then both peptides are reacted. The thus obtained inhibitor for cleavage of CaNA can be purified with the above-mentioned purification method.

The suppressant for neuronal cell death of the present invention means an agent which comprises the above-mentioned inhibitor for cleavage of CaNA by calpain as an active ingredient, and inhibits long term induction of neuronal cell death in neuronal cells. The suppressant for neuronal cell death can be also used as an agent for preventing or treating a disease related to neuronal cell death. The suppressant for neuronal cell death of the present invention preferably contains the inhibitor for cleavage of CaNA comprising the peptide of SEQ No. 2 and the intracellular transporting signal peptide, and more preferably contains the inhibitor for cleavage of CaNA comprising the peptide of SEQ No. 1, the peptide of SEQ No. 2 and an intracellular transporting signal peptide. The above-mentioned agent for preventing or treating a disease related to neuronal cell death means a pharmaceutical preparation comprising an effective amount of the suppressant for neuronal cell death for preventing or treating the disease related to neuronal cell death. The disease related to neuronal cell death includes, for example, Alzheimer's disease, dementia, brain ischemic disease, intracerebral hemorrhage such as subarachnoid hemorrhage, spinal injury (trauma), Parkinson disease, epilepsy, and the like.

As an administration route of the suppressant for neuronal cell death of the present invention, there include, for example, oral administration, intravenous administration, intracerebral direct administration and the like. The oral administration is preferable in the light of a burden on a patient and the side effect.

A dosage form of the suppressant for neuronal cell death of the present invention can be appropriately set depending on the administering method. Concretely, there include liquid formulations such as solution, emulsion and suspension, tablet, capsule, and the like. For example, in case of oral administration, tablet or capsule formulation is preferable, in case of intravenous administration or intracerebral directly administration, the liquid formulation is preferable. Various additives usually used by a person skilled in the art according to the dosage form can be used for formulating the suppressant for neuronal cell death of the present invention. Such additives include an antioxidant, pH adjustment, preservative and the like.

The dosage of the above-mentioned suppressant for neuronal cell death can be appropriately set depending on the administration method, age, weight and condition of the patient to be applied, and the like. For instance, the dosage is preferably at least 0.1 mg/kg/day as the inhibitor for cleavage of the CaNA by calpain of the present invention, and more preferably at least 1 mg/kg/day. When the dosage is less than 0.1 mg/kg, it tends to reduce the inhibitory effect on cleavage of CaNA by half. Moreover, the dosage is preferably 100 mg/kg/day or less as the inhibitor for cleavage of the CaNA by calpain of the present invention, and more preferably 20 mg/kg/day or less. When the dosage exceeds 100 mg/kg, it tends to show the cell toxicity. The suppressant for neuronal cell death of the present invention can be administered by either single dose or multiple doses.

An additive for a culture medium of cells and brain slice comprising of the present invention means the additive for the culture medium containing at least the inhibitor for cleavage of CaNA. The additive for the culture medium of cell and brain slice comprising the present invention preferably contains the inhibitor for cleavage of CaNA comprising the peptide of SEQ No. 2 and the intracellular transporting signal peptide, and more preferably contains the inhibitor for cleavage of CaNA comprising the peptide of SEQ No. 1, the peptide of SEQ No. 2 and an intracellular transporting signal peptide.

When the inhibitor for cleavage of CaNA by calpain of the present invention is applied to culture cells, the amount of addition is preferably 0.01 to 100 nmol/ml, and more preferably 0.1 to 10 nmol/ml in the culture medium having the cell concentration of $1 \times 10^5$ cell/ml. When the amount of addition is less than 0.01 nmol/ml, it tends to reduce the inhibitory effect on cleavage of CaNA by half, and when it is more than 100 nmol/ml, it tends to show the cell toxicity.

The present invention is explained in more detail by means of the following Examples, but the present invention is not limited thereto.

EXAMPLE 1

In order to introduce FDGATAAARKEVIRNK (SEQ No. 1) and REESESVLTLKGLTPTG (SEQ No. 2) as the inhibitor for cleavage of CaNA of the present invention into the cultured cells, the following oligopeptides in which the intracellular introducing signal peptide (ten arginines) was added to their N terminal were prepared (available from PEPTIDE INSTITUTE INC.).

```
RRRRRRRRRRFDGATAAARKEVIRNK      (SEQ No. 5)

RRRRRRRRRRREESESVLTLKGLTPTG     (SEQ No. 6)
```

(Preparation of Neuronal Cells)

After the brain hippocampus from 18 days embryo of Wister rat had been removed, it was treated with PBS containing 0.05% trypsin for 15 minutes at 37° C. After the neuronal cells were suspended with a glass pipet, $1 \times 10^6$ cells were cultured in a 3.5 cm diameter culture dish which was previously coated with poly-D-lysine. As the medium, 3 ml Neuro Basal medium (available from Invitrogen, Inc.) complemented with B27 supplement (0.03 ml; available from Invitrogen, Inc.), penicillin (100 units/ml in the final concentration; available from Invitrogen, Inc.) and streptomycin (100 μg/ml in the final concentration; available from Invitrogen, Inc.) was used and the cultivation was carried out in carbon dioxide incubator (5% $CO_2$, 37° C.).

(Addition of Peptide)

The peptides of above-mentioned SEQ Nos. 5 and 6 were added in the culture solution with the final concentration of 1 μM 10 days after beginning of culture, and it was incubated in carbon dioxide incubator (5% $CO_2$, 37° C.). Three hours after the addition, glutamic acid was added in the final concentration of 500 μM, and it was incubated for 15 minutes. The culture solution was then exchanged, and it was further cultured. The cells were collected at 3 hours and 24 hours after glutamic acid was added, were disrupted by ultrasonic wave in 1% SDS solution, and the SDS-PAGE buffer was added thereto. After this sample was subjected to the SDS-PAGE gel electrophoresis, Western blotting was carried out using the antibody recognizing CaNA (rabbit serum, available form Santa Cruz Biotechnology, Inc). In this Example, a cell sample in which neither glutamic acid nor the cleavage inhibiting peptide was added was used as a control. Moreover, the cell sample in which only glutamic acid was added and the cell sample in which only the cleavage inhibiting peptide was added were concurrently prepared.

Figure 1B:
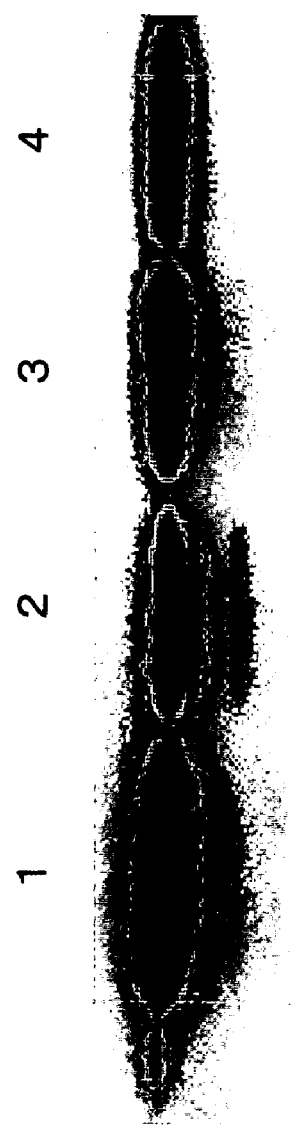
FIG. 1(b) shows the result of the sample which was incubated for 24 hours after the addition of glutamic acid.

The result was shown in FIG. 1. In the glutamic acid addition group, the fragmentation of calcineurin was observed. On the other hand, in the neuronal cells treated with the cleavage inhibiting peptide, cleavage of calcineurin which was able usually to be caused by the addition of glutamic acid was inhibited.

EXAMPLE 2

The neuronal cells were cultured in the same manner as in Example 1, and then the above-mentioned peptides of SEQ Nos. 5 and 6 were added in the final concentration of 1 μM in the same manner as in Example 1. The calcineurin inhibitor, FK506 (available from Fujisawa pharmaceutical Co., Ltd.; the final concentration of 1 μM) or calpain inhibitor, ALLM (available from Merck & Co., Inc.; the final concentration of 25 μM) was added as a control. After 2 hours incubation with each reagent, glutamic acid was added in the final concentration of 500 μM, followed by 15 minutes incubation. The culture solution was then exchanged, and it was further cultured. Each neuronal cell was fixed with 4% paraformaldehyde 3, 6, 12 or 24 hours after the addition. Thereafter, TUNEL staining (available from Roche Diagnostics, Inc) was carried out to identify the neuronal cells which caused cell death. The TUNEL positive cell was counted.

Figure 2:
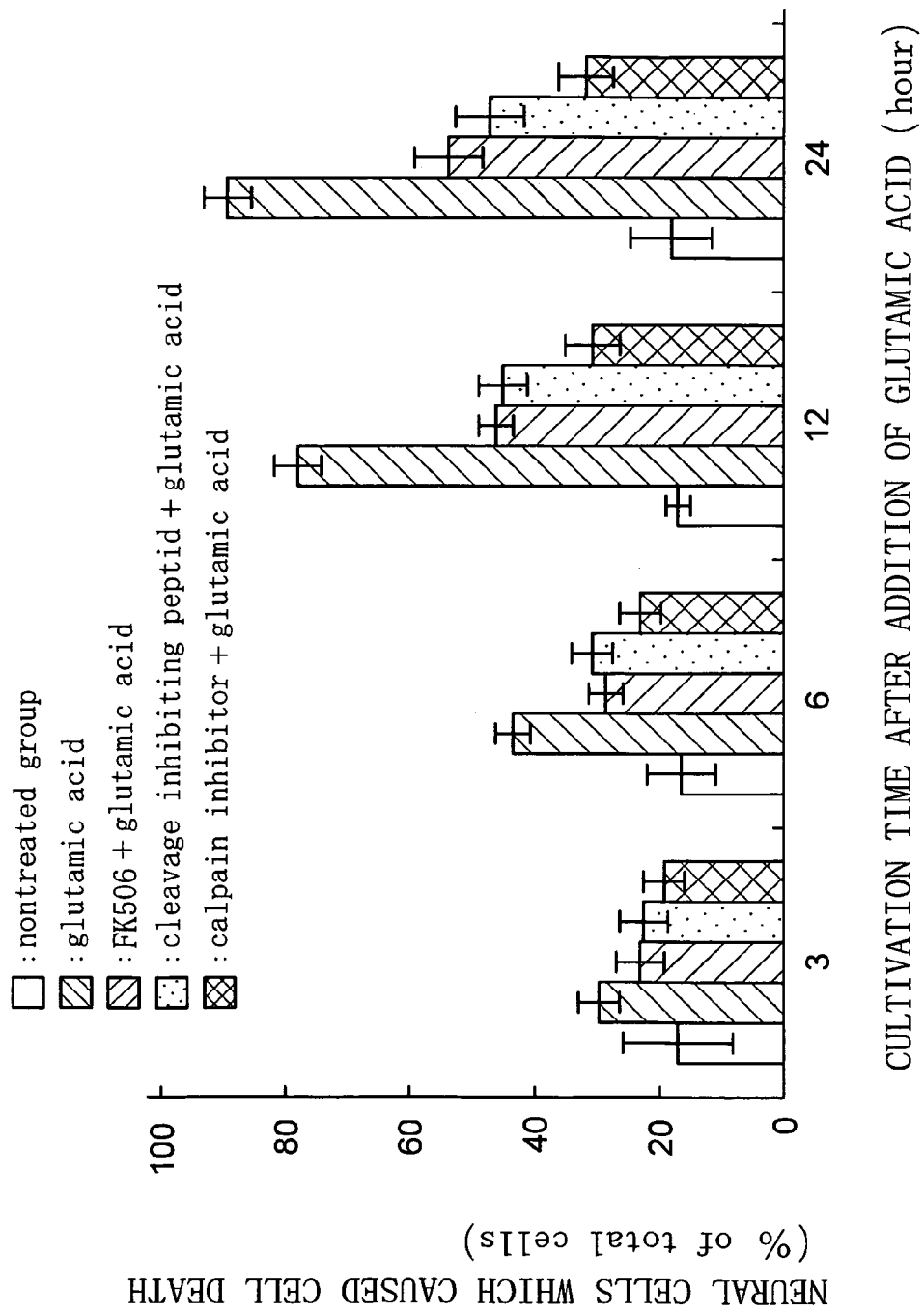
FIG. 2 shows the number of neuronal cells in which neuronal cell death was induced by adding glutamic acid.

The result is shown in FIG. 2. In the glutamic acid addition group, the number of the neural cells which caused cell death increased with the time course after the administration. It was demonstrated that the cleavage inhibiting peptide had the suppressive effect on neuronal cell death induced by glutamic acid. Moreover, the effect was the same degree as that of FK506 or ALLM.

REFERENCE EXAMPLE 1

Calcineurin 1 μM refined from cow brain was reacted with 1 μM of calmodulin (available from Merck & Co., Inc.) and/or 1 μM of m-calpain (available from Merck & Co., Inc.) in a reacting solution (containing 20 mM Tris-HCl, pH 7.4, 1 mM $CaCl_2$, and 1 mM $MgCl_2$) at 30° C. for one hour, respectively. After the reaction 12% SDS-PAGE gel electrophoresis was carried out and then said gel was stained with Coomassie blue.

As a result, in case that the calpain was not added, the purified CaNA was seen at the size of 60 kDa on the electrophoresis. This is corresponding to the size of CaNA that has been reported up to now. On the other hand, in case that calmodulin and calpain were added, the band was not observed at 60 kDa but was observed at 48 and 45 kDa. In case that calcineurin was reacted with only calpain, the cleaved CaNA in the size of 45 kDa was observed.

As the above-mentioned result it is clear that calcineurin is cleaved by calpain.

In addition, as determining the cleavage site of CaNA by calpain, the cleaved protein of 45 kDa was composed of the amino acids up to 392 in the amino acid sequence and the cleaved protein of 48 kDa was composed of amino acids up to 421, up to 422, up to 423 and up to 424 in the amino acid sequence.

INDUSTRIAL APPLICABILITY

This invention provied the inhibitor for cleavage of CaNA. The inhibitor for cleavage of CaNA of the present invention can suppresses neuronal cell death caused by the activation of calcineurin, because it can inhibit the constitutive active forming of calcineurin. Moreover, a suppressant for neuronal cell death of the present invention contianing the inhibitor for cleavage of CaNA is excellent useful because it can be used as a drug for prevention or treatment of the disease associated with neuronal cell death including the dementia disease and the like. In addition, if the additive of the culture medium for cells of the present invention containing the inhibitor for cleavage of CaNA is used, the cultured cell can be grown well. Moreover, the inhibitor for cleavage of CaNA of the present invention can be also used as a reagent for the investigation about neuronal cell death.

SEQUENCE LISTING FREE TEXT

SEQ No. 5: Peptide sequence consisting of peptide sequence derived from human and artificial peptide sequence.

SEQ No. 6: Peptide sequence consisting of peptide sequence derived from human and artificial peptide sequence.

The invention claimed is:

1. An inhibitor for cleavage of calcineurin subunit A by calpain, which consists of a peptide selected from the group consisting of SEQ ID NOs. 1, 2, 5 or 6.

2. An inhibitor for cleavage of calcineurin subunit A by calpain which consists of the peptides SEQ ID NOs. 1 and 2.

3. An inhibitor for cleavage of calcineurin subunit A by calpain which consists of the peptides SEQ ID NOs. 5 and 6.

4. An additive for a culture medium of a cell or a brain slice consisting of the inhibitor for cleavage of calcineurin subunit A of claims 1, 2, or 3.

* * * * *